United States Patent
Brown et al.

(10) Patent No.: US 11,408,430 B2
(45) Date of Patent: Aug. 9, 2022

(54) MODULAR FAN ASSEMBLY

(71) Applicant: SharkNinja Operating LLC, Needham, MA (US)

(72) Inventors: Andre D. Brown, Natick, MA (US); Jason B. Thorne, Wellesley Hills, MA (US); Peter Hutchinson, Suzhou (CN); Gary Palladino, Sommerville, MA (US); Alden Kelsey, Newton, MA (US); Daniel J. Innes, West Roxbury, MA (US); Zach Hellman, Newton, MA (US); Josh Anthony, Needham, MA (US); Sunil Moda, Needham, MA (US); Lloyd Olson, Needham, MA (US); Ramiro Henriquez Porras, Needham, MA (US); Da Deng, Needham, MA (US)

(73) Assignee: SharkNinja Operating LLC, Needham, MA (US)

( * ) Notice: Subject to any disclaimer, the term of this patent is extended or adjusted under 35 U.S.C. 154(b) by 908 days.

(21) Appl. No.: 16/137,162

(22) Filed: Sep. 20, 2018

(65) Prior Publication Data
US 2019/0085852 A1    Mar. 21, 2019

Related U.S. Application Data

(60) Provisional application No. 62/561,597, filed on Sep. 21, 2017.

(51) Int. Cl.
*F04D 25/08*       (2006.01)
*F04D 29/40*       (2006.01)
(Continued)

(52) U.S. Cl.
CPC ............ *F04D 25/08* (2013.01); *A47L 9/0063* (2013.01); *A47L 9/20* (2013.01); *A47L 9/281* (2013.01);
(Continued)

(58) Field of Classification Search
CPC .......... F04D 25/08; A47L 9/0063; A47L 9/20; A47L 9/281
(Continued)

(56) References Cited

U.S. PATENT DOCUMENTS

2008/0206092 A1    8/2008   Crapser et al.
2014/0365018 A1*  12/2014  Kusukame ......... G05D 23/1917
                                                                    700/276
(Continued)

FOREIGN PATENT DOCUMENTS

JP    H07017241 U    3/1995
JP    2017122554 A   7/2017

OTHER PUBLICATIONS

Erdingerl, L., et al. "Improving indoor air quality in dental practices and certain hospital environments with stand-alone air purification systems." University of Heidelberg, pp. 1-5. Accessed from https://www.aivc.org/sites/default/files/members_area/medias/pdf/Conf/1999/paper082.pdf (Year: 1999).*

(Continued)

*Primary Examiner* — Satish Rampuria
(74) *Attorney, Agent, or Firm* — Mintz Levin Cohn Ferris Glovsky and Popeo, PC; Lisa Adams

(57) ABSTRACT

In accordance with the present disclosure a modular air treatment system is disclosed. The modular air treatment system includes a fan apparatus having a base to removably couple to at least one of an air filter and/or a humidifier, (Continued)

wherein the fan apparatus includes a fan body with at least one convex surface and a nozzle to output air along the at least one convex surface.

13 Claims, 16 Drawing Sheets

(51) Int. Cl.
| | |
|---|---|
| *F04D 27/00* | (2006.01) |
| *G05D 1/00* | (2006.01) |
| *A47L 9/00* | (2006.01) |
| *A47L 9/20* | (2006.01) |
| *B01D 46/00* | (2022.01) |
| *A47L 9/28* | (2006.01) |
| *F04D 29/70* | (2006.01) |
| *A61L 9/12* | (2006.01) |
| *F24F 11/79* | (2018.01) |
| *A47L 9/10* | (2006.01) |
| *A47L 9/12* | (2006.01) |

(52) U.S. Cl.
CPC ........... *A47L 9/2826* (2013.01); *A47L 9/2894* (2013.01); *A61L 9/122* (2013.01); *B01D 46/0028* (2013.01); *B01D 46/0038* (2013.01); *B01D 46/0041* (2013.01); *F04D 27/00* (2013.01); *F04D 29/403* (2013.01); *F04D 29/701* (2013.01); *F24F 11/79* (2018.01); *G05D 1/0011* (2013.01); *A47L 9/106* (2013.01); *A47L 9/12* (2013.01); *A47L 2201/022* (2013.01); *A47L 2201/04* (2013.01); *B01D 2279/40* (2013.01); *B01D 2279/55* (2013.01); *G05D 2201/0203* (2013.01)

(58) Field of Classification Search
USPC .................................................. 700/275–285
See application file for complete search history.

(56) References Cited

U.S. PATENT DOCUMENTS

2017/0196425 A1* 7/2017 Brown .................... A47L 9/165
2019/0032932 A1* 1/2019 Xing ..................... A47L 9/2873

OTHER PUBLICATIONS

Birmingham, Joseph G., and Gautam Pillay. "Air purification in chemical and biological warfare environments using gas-phase corona reactor technology." Terrorism and Counter-Terrorism Methods and Technologies. vol. 2933. International Society for Optics and Photonics, 1997.pp. 126-132 (Year: 1997).*

Kim, Seong-Uck, and Chang-Sun Kang. "Evaluation of radioactive source terms in the system-integrated modular advanced reactor." Nuclear Engineering and Technology 31.1 (1999): pp. 9-16. (Year: 1999).*

International Search Report issued in Application No. PCT/US2018/052177; International Filing Date Sep. 21, 2018; dated Feb. 25, 2019, 7 pages.

Written Opinion of the International Searching Authority issued in Application No. PCT/US2018/052177, International Filing Date Sep. 21, 2018, dated Feb. 25, 2019, 8 pages.

* cited by examiner

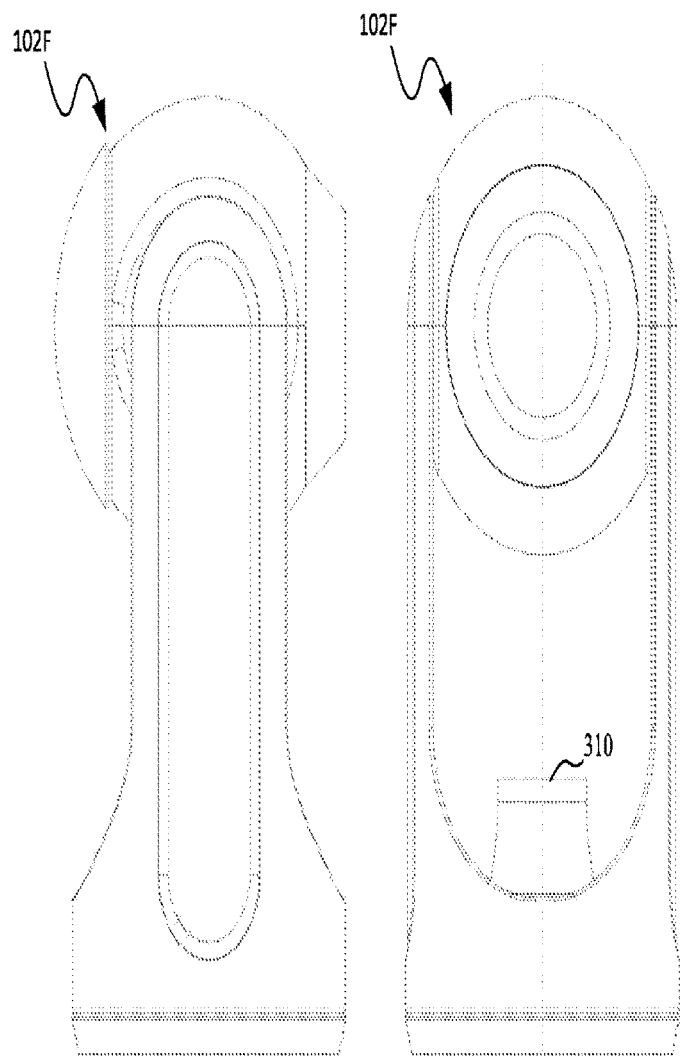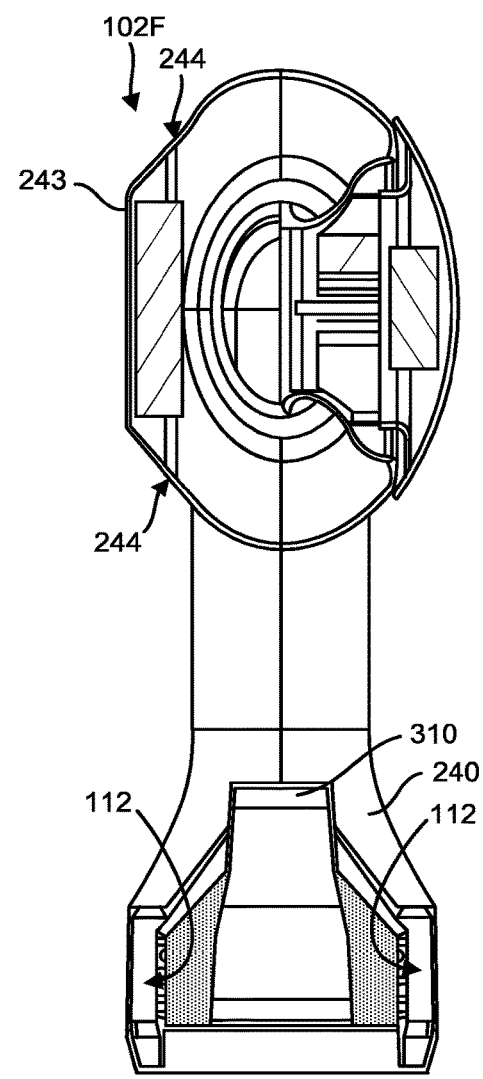
FIG. 12A     FIG. 12B     FIG. 12C

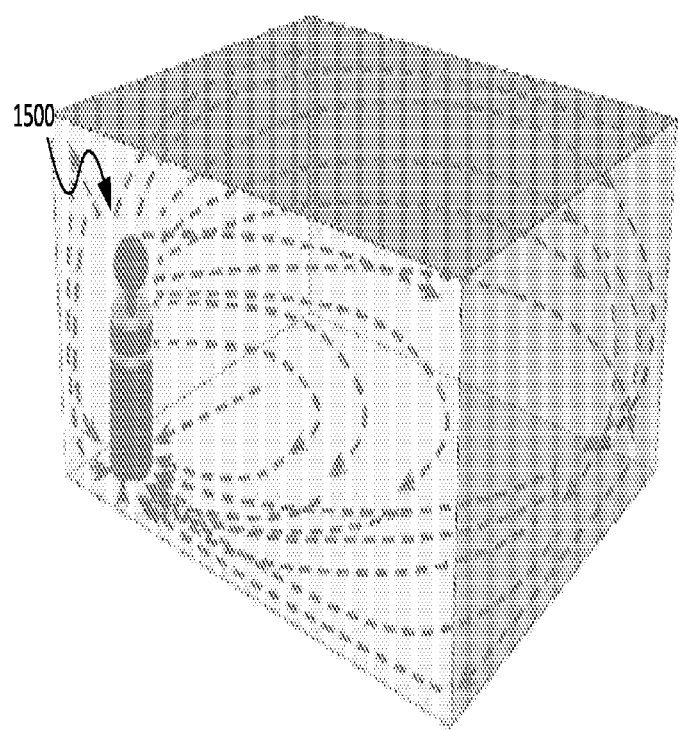
FIG. 17A
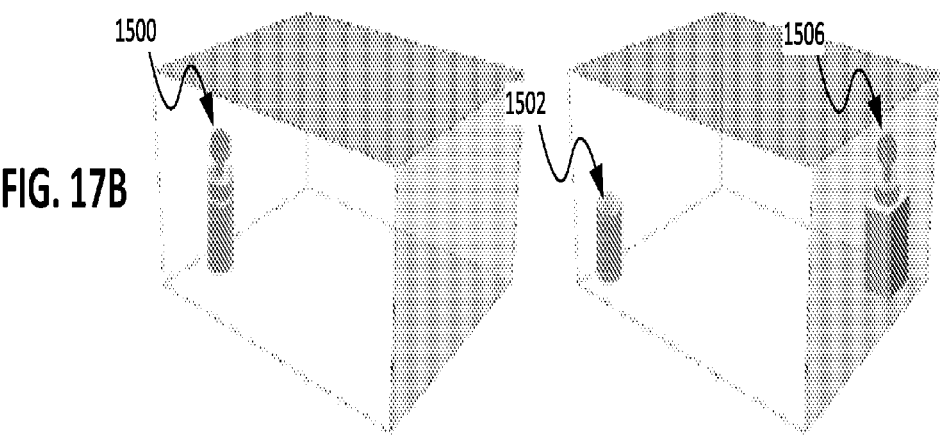
FIG. 17B
FIG. 17C

MODULAR FAN ASSEMBLY

CROSS-REFERENCE TO RELATED APPLICATIONS

This application claims the benefit of U.S. Provisional Application Ser. No. 62/561,597, filed Sep. 21, 2017, which is incorporated herein by reference in its entirety.

TECHNICAL FIELD

This specification relates to air treatment systems, and more particularly, to a modular fan assembly which can attach to one or more air treatment assemblies such as a humidifier and/or an air filter.

BACKGROUND INFORMATION

The following is not an admission that anything discussed below is part of the prior art or part of the common general knowledge of a person skilled in the art.

Fan assemblies may be used to generate air flow in various environments such as homes and offices. Fans often include a mechanism that allows a user to redirect air output in a desired location by applying a user-supplied force to rotate/tilt the fan to a desired position. Also, fans often include a feature that allows the fan to horizontally span/sweep right-to-left automatically to target a larger area within a given environment.

Some fan assemblies offer integrated humidification devices which may include a water reservoir proximate to a fan/impeller of the fan assembly. Moisture may then be introduced by exposing the impeller to water droplets/vapor. However, exposure of the impeller and other internal workings of the fan to water vapor/droplets may promote the growth of bacteria/mold. As a result, the fan may then output foul smelling and/or air which is harmful to occupants in the environment.

While known fan apparatuses are generally effective at increasing air circulation, such fans remain at a fixed position and are unable to adjust to varying conditions in the environment. Moreover, fans may inadvertently circulate air which includes harmful bacterial and/or foul smelling particles.

BRIEF DESCRIPTION OF THE DRAWINGS

These and other features advantages will be better understood by reading the following detailed description, taken together with the drawings wherein:

FIGS. 12A-12C show an additional example configuration for an air treatment system, in accordance with an embodiment of the present disclosure.

FIGS. 17A-17C show various embodiments of an air treatment system consistent with the present disclosure.

The drawings included herewith are for illustrating various examples of articles, methods, and apparatuses of the teaching of the present specification and are not intended to limit the scope of what is taught in any way.

DETAILED DESCRIPTION

Various apparatuses or processes will be described below to provide an example of an embodiment of each claimed invention. No embodiment described below limits any claimed invention and any claimed invention may cover processes or apparatuses that differ from those described below. The claimed inventions are not limited to apparatuses or processes having all of the features of any one apparatus or process described below or to features common to multiple or all of the apparatuses described below. It is possible that an apparatus or process described below is not an embodiment of any claimed invention. Any invention disclosed in an apparatus or process described below that is not claimed in this document may be the subject matter of another protective instrument, for example, a continuing patent application, and the applicants, inventors or owners do not intend to abandon, disclaim or dedicate to the public any such invention by its disclosure in this document.

Figure 1:
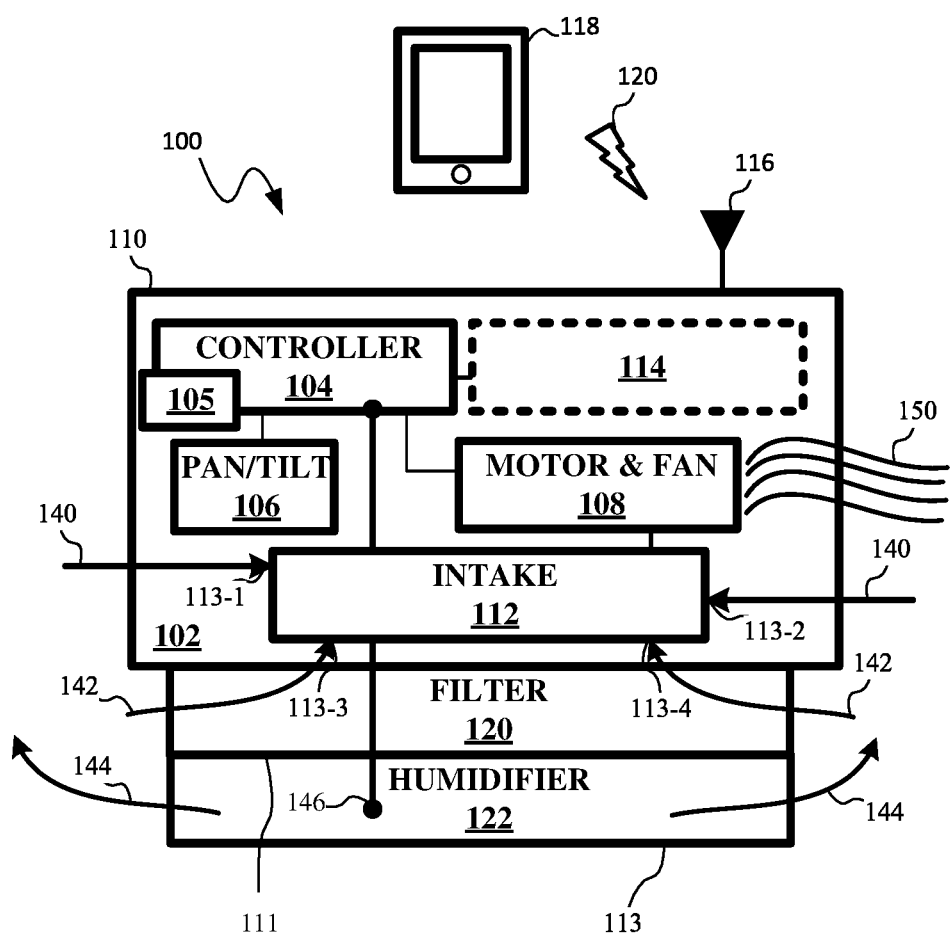
FIG. 1 shows a block diagram of an example air treatment system in accordance with an embodiment of the present disclosure.

Turning now to FIG. 1 one embodiment of an air treatment system 100 is shown in accordance with aspects of the present disclosure. As shown, the air treatment system 100 includes a fan apparatus 102 (or modular fan apparatus 102) removably coupled to an optional air filter 120, and an optional humidifier 122. Note that the optional air filter 120 and the optional humidifier 122 may be coupled in a different order, such as shown in FIGS. 13A-13D where the humidifier 122 is coupled between the filter 120 and the base 240 of the fan apparatus 102. The fan apparatus 102 may include a single housing 110 or may optionally comprise a plurality of housing portions. Each of the optional humidifier 122 and the air filter 120 may both electrically and fluidly couple with the fan apparatus 102, although this disclosure is not limited in this regard. For example, and as discussed further below, the humidifier 122 may not necessarily be in direct fluid communication (e.g., via one or more passageways therebetween) and may instead be indirectly fluidly coupled by virtue of the humidifier outputting humidified air externally which may then be received by the fan apparatus via, for instance, inlet ports 113-1 and 113-2. Humidifier may include a plurality of fluid couplings, including air, water, emulsions of air and water, and purified air received from the air purifier module.

The fan apparatus 102 includes a controller 104, a pan/tilt mechanism 106, a motor and fan assembly 108, and an air intake 112. The fan apparatus 102 may also include an antenna device 116. The antenna device 116 (which may also be referred to as a network interface) may be configured to communicate with, for instance, one or more user devices such as the user device 118. The user device 118 may include a so-called "app" for controlling operation of the air treatment system 100, which will be discussed in greater detail below. The fan apparatus 102 may therefore communicate with the user device 118 via a wireless connection.

To this end, air treatment system 100 may be configured for close range or long range communication between the fan apparatus 102 and the user device 118. The term, "close range communication" is used herein to refer to systems and methods for wirelessly sending/receiving data signals between devices that are relatively close to one another. Close range communication includes, for example, communication between devices using a BLUETOOTH™ network, a personal area network (PAN), near field communication, ZigBee networks, a Wi-Fi network (e.g., IEE 802.11X) millimeter wave communication, ultra-high frequency (UHF) communication, combinations thereof, and the like. Close range communication may therefore be understood as enabling direct communication between devices, without the need for intervening hardware/systems such as routers, cell towers, internet service providers, and the like.

The controller 104 comprises at least one processing device/circuit such as, for example, a digital signal processor (DSP), a field-programmable gate array (FPGA), Reduced Instruction Set Computer (RISC) processor, x86 instruction set processor, microcontroller, an application-specific integrated circuit (ASIC). The controller 104 may be implemented, for example, using software (e.g., C or C++ executing on the controller/processor 104), hardware (e.g., hardcoded gate level logic or purpose-built silicon) or firmware (e.g., embedded routines executing on a microcontroller), or any combination thereof. The controller 104 may further include a memory 105. The memory 105 may comprise, for example, volatile and/or non-volatile memory. The memory 105 may include operational settings/parameters such as fans speed, heating/cool modes, aromatic selection properties, scheduling, voice recognition profiles, and/or face recognition profiles. Each of the operational settings may be adjusted remotely via an "app" executed on the user device 118, for instance. The memory 105 may also include air particle quality measurements, fan scheduling. The app may further allow for displaying of data logged from the fan apparatus. Such logged data may include periodic temperature measurements, particle count data, and so on.

The pan/tilt mechanism 106 may comprise one or more mechanisms for horizontal and/or vertical adjustment of the portion of the housing 110 including the motor and fan 108. For instance, the pan/tilt mechanism 106 may be configured to adjust the yaw/pitch based on user input (e.g., from the user device 118). Accordingly, the pan/tilt mechanism 106 allows the fan apparatus 102 to adjust both along a horizontal and/or vertical axis to provide up to 360 degrees of motion for each axis thus forming a spherical coverage envelop.

The motor and fan 108 may output air 150 and may be any suitable motor and fan for providing a desired amount of air volume and air flow speed. The motor of the motor and fan 108 may be variable (e.g., a DC stepper motor, or a brushless DC motor) for adjusting fan speed during operation.

The intake 112 may include one or more ducts/passageways for providing air to the motor and fan 108. The intake 112 may include a plurality of intake ports including intake ports 113-1 and 113-2. Intake ports 113-1 and 113-2 may be configured to receive air 140 external to the housing 110. In some cases, the intake ports 113-1 and 113-2 may be disposed on opposite sides of the housing 110.

The intake 112 may further include intake ports 113-3 and 113-4. Intake ports 113-3 and 113-4 may be configured to receive air 142 from the filter 120. In such cases, the air 142 may be accurately referred to as filtered air. In an embodiment, the presence of the filter 120 coupled to the housing 110 causes the intake ports 113-1 and 113-2 to mechanically close. Therefore, intake ports 113-1 and 113-2 may be entirely closed or at least substantially closed, e.g., restricting input from external air 140 to less than 10%. Thus, the fan apparatus 102 may receive only filtered air 142 for output by the motor and fan 108 in some embodiments.

In any event, the filter 120 may include a housing 111. The housing 111 may include a portion configured to removably couple to the housing 110 of the fan apparatus 102. The filter 120 may include, for instance, a HEPA filter for removing allergens, dust and/or other contaminants in an environment. The filter 120 may include a removable filter portion for easy replacement.

The humidifier 122 may include a housing 113. The housing 113 may include a portion configured to removably couple to the housing 111 of the filter 120 and/or couple (e.g., directly) to the housing 110 of the fan apparatus 102. The humidifier 122 may include one or more a water reservoirs (not shown) and an assembly for dispersing water droplets/vapor into the air via air 144. The humidifier 122 may include circuitry (not shown) to output a desired amount of water vapor into an environment. In some cases, the humidifier 122 electrically couples via bus 146 to the controller 104. The humidifier 122 may receive signals from the controller 104 by way of the bus 146 to control the amount of water vapor output and the amount of time to output water vapor (e.g., based on a schedule). In an embodiment, relative humidity may be periodically measured and may be optionally displayed via an app on the user device 118. In response to humidity exceeding a predefined threshold, fan speed and/or the humidifier output may be adjusted to reach a target humidity (e.g., a user defined humidity level set via the app of the user device 118).

In some embodiments, and as shown, the humidifier 122 is not in fluid communication with the fan apparatus 102. In this case, the humidified air 144 output by the humidifier 122 is external to the fan apparatus 102. The humidified air 144 may then be received by the fan apparatus 102 via intake ports 113-1 and 113-2 and/or intake ports 113-3 and 113-4 (in cases where the filter 120 is present). Thus, the growth of bacterial/mold on the motor and fan 108 may be eliminated as the fan simply receives filtered air rather than humidified air containing water droplets which other integrated fan solutions utilize, as previously discussed above.

Figure 3:
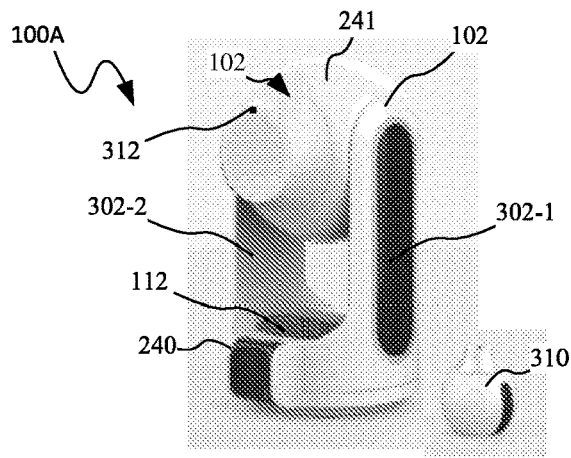
FIGS. 3-5 show an example configuration of an air treatment system in accordance with embodiments of the present disclosure.

The fan apparatus 102 may further include additional circuitry 114. Additional circuitry 114 may include, for example, one or more image sensors/cameras. One example image sensor 312 is shown in FIG. 3. For example, the one or more image sensors may output color image data (RGB), color and depth image data (RGBD camera), depth sensor information, stereo camera information (L/R RGB), YUV, infrared signals, and so on. For example, the additional circuitry 114 may include a first sensor being an infrared detector and a second sensor being a color-image sensor (e.g., RGB, YUV). In one example, the fan apparatus 102 includes a first image sensor configured for capturing an image signal (e.g., color image sensor, depth-enabled image sensing (RGDB), stereo camera (L/R RGB), YUV, infrared, and x-ray) and a second image sensor configured to capture image data different from the first image sensor.

In an embodiment, the fan apparatus 102 compares image data received from the one or more image sensors to data within memory 105 to, for example, recognize a particular user present in an environment. In this embodiment, the controller 104 may implement a known facial recognition algorithm to recognize a user. In the event a user is recognized, the fan apparatus 102 may automatically begin output of air 150 based on a user profile. The user profile may include a preferred fan speed, a preferred fragrance preference, and/or whether the fan apparatus 102 should output air 150 directly at a recognized user's position in a room not, as the case may be.

Note that this disclosure is not necessarily limited to tracking only "identified" users. For instance, in some cases the fan apparatus 102 may pan/tilt, e.g., via the pan/tile mechanism 106, to move to follow any person in an environment as they move around.

In an embodiment, the image data processed by the fan apparatus 102 may also include thermal (e.g., infrared) image data, as discussed above. In this embodiment, the fan apparatus 102 may thermally map a room to identify areas of interest for cooling/heating purposes. For instance, if warm air is found to be in pockets (e.g., the corner of a ceiling), the fan apparatus 102 may identify the spot and direct air flow in that general direction to bring the temperature down.

Figure 8:
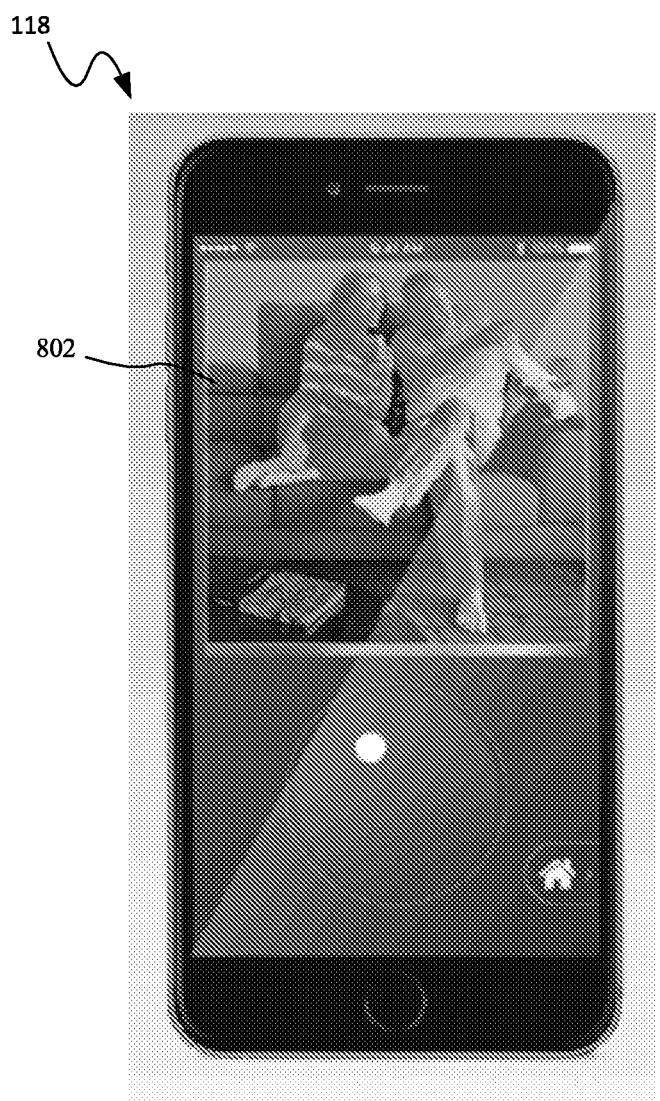
FIG. 8 shows thermal image data on a user device received from an air treatment system, in accordance with an embodiment of the present disclosure.

The thermal map may also extend to people/pets in a room. For example, the heat signature of a user may be utilized to determine if the fan apparatus 102 should direct air in that user's direction. In this example, a person who appears relatively hot (e.g., having just come indoors on a hot summers day) may cause the fan apparatus 102 to register the heat signature as needing cooling and direct air accordingly. In some cases, the fan apparatus 102 provides the thermal data to the user device 118, such as shown in FIG. 8. In this case, the user may utilize the visualized thermal image data 802 to "train" the app in order to cause the fan apparatus 102 to provide heating/cooling depending on a person's registered heat signature. The thermal image data sent to the user device 118 may also allow a user to recognize spots in their home/office where heat may be entering (e.g., via a crack, window, or other opening) or where heat/cold air is escaping. Such information may be useful for detecting and fixing leaks in an environment.

The additional circuitry may further include a microphone sensor for receiving voice input commands from a user. For example, the fan apparatus 102 may receive voice commands such as "fan on" to cause the fan to begin circulating air in a surrounding environment. In another example, the fan apparatus 102 may include a voice command such as "fan on me" to cause the fan to target (e.g., via rotation by pan/tilt mechanism 106) the user who spoke the command to direct air flow in their general direction. Likewise, "fan off me" or "fan move left/right/up/down" may further be suitable voice commands for adjusting operation of the fan apparatus 102. Voice commands may also be utilized to change fan speed of the motor and fan 108 and/or may be utilized to select a particular output fragrance.

In some cases, the user device 118 may receive/capture the voice commands via a local microphone and transmit the same to the fan apparatus 102 to cause the same to change operation accordingly.

Figure 2:
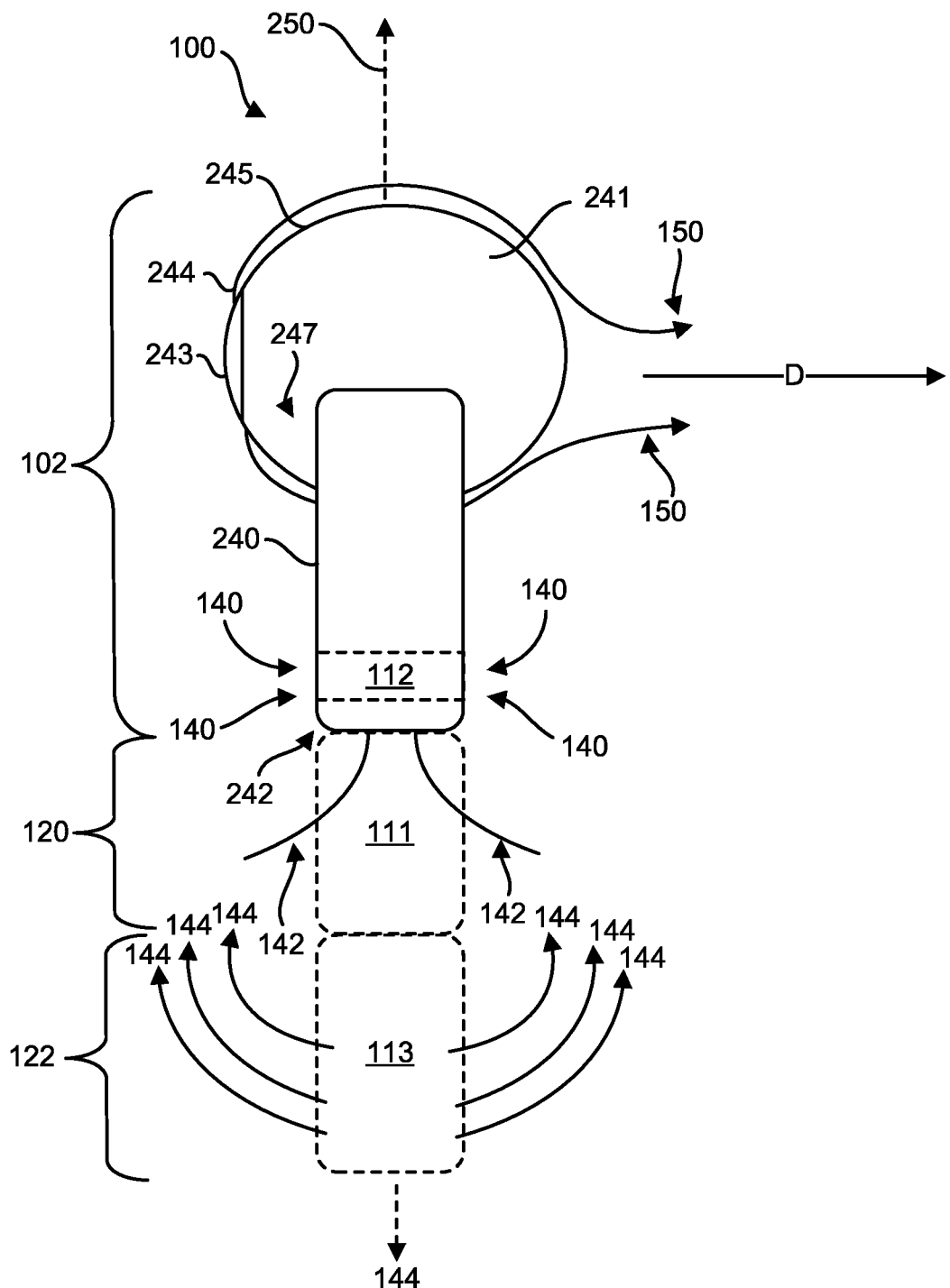
FIG. 2 shows another example block diagram of the example air treatment system of FIG. 1, in accordance with an embodiment of the present disclosure.

Turning to FIG. 2, a block diagram shows a side view of the air treatment system 100 in accordance with various aspects and embodiments of the present disclosure. As shown, the fan apparatus 102 includes a housing comprised of a base portion 240 and a spheroid fan portion 241 (or fan body 241). In some embodiment, the base portion 240 includes at least two arms extending therefrom to hold the fan body 241 securely in position, which are better shown in FIGS. 3-5. However, the base portion 240 may include less arms, e.g., one arm as shown in the embodiment of FIGS. 14A-14G, or more than two arms depending on a desired configuration. A first end 242, or module coupling end, of the base portion 240 may include a coupling receptacle for coupling with the optional filter 120 and/or optional humidifier 122. A portion of the pant/title mechanism 106 may be disposed adjacent the module coupling end 242 and may allow the base 240, and by extension the fan body 241, to rotate about the longitudinal axis 250 (e.g., to provide movement/rotation along a horizontal axis).

A second end 247, or fan coupling end, of the base portion 240 may couple to the fan body 241. The fan body 241 may couple to base 240 by a second portion of the pan/title mechanism 106, with the second portion of the pan/title mechanism 106 allowing for up/down movement, or more particularly, movement along the longitudinal axis 250. Thus, the pan/tilt mechanism 106 of the fan apparatus 102 allows for 360 degrees of movement to direct output air 150 towards virtually any location within an environment.

The fan body 241 is not necessarily limited to a sphere shape and may instead comprise any regular or irregular shape that provides at least one convex surface. For example, the fan body 241 may comprise an ellipsoid, oval or sphere, although these examples are not intended to be limiting.

In any event, the fan body 241 includes a nozzle 243 which defines at least one outlet 244, with the nozzle 243 being configured to output air 150 along convex surface 245. As shown, the Coanda effect results in air 150 generally following convex surface 245 such that the air is generally is substantially output in direction D. Accordingly, air 150 may travel externally and not necessarily through a passageway provided through the fan body 241.

The intake 112 may be adjacent the module coupling end 242. The intake 112 may be fluidly coupled via one or more passageways within the base 240 which extend substantially in parallel with the longitudinal axis 250.

Figure 4:
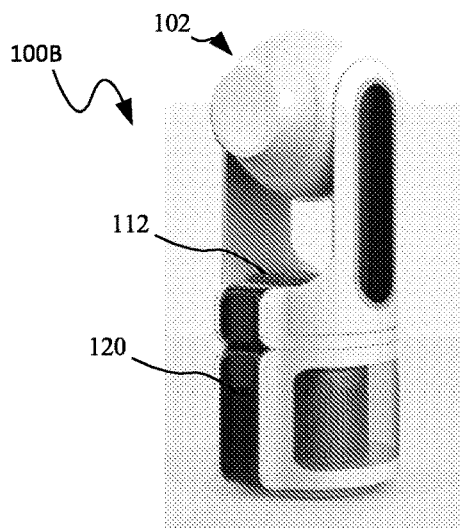
Figure 5:
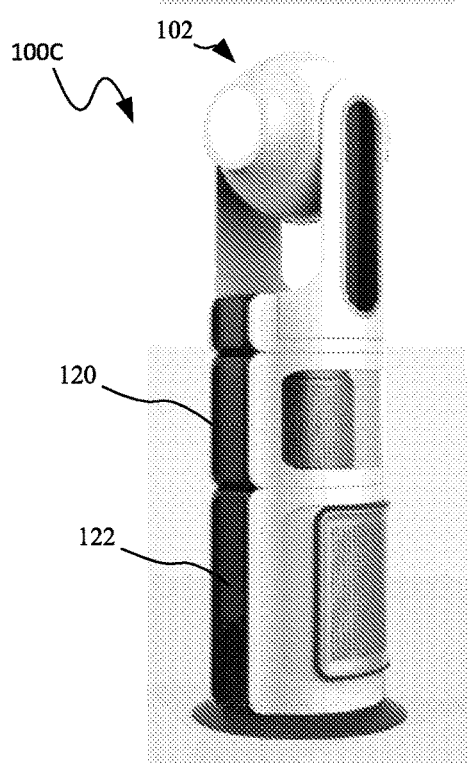

Referring to FIGS. 3-5 the air treatment system is shown in accordance with embodiments disclosed herein. FIG. 3 shows an air treatment system 100A including only the fan apparatus 102. As shown, intake 112 includes at least one semi-permeable region (e.g., a mesh) to receive air, e.g., air 140. Air 140 may then be provided via passageways/channels in one or both of arms 302-1, 302-2 to the fan body 241. As shown, a fragrance unit 310 (or fragrance diffuser) may be placed on (or adjacent) the intake 112 and output an adjustable amount of fragrance towards the bottom of the fan body 241. Air, e.g., air 150, output by the nozzle 243 may then combine with the fragrance and thus cause air 150 to have a predefined scent. The fragrance unit 310 may include one or more scents (e.g., provided by oils or gels or fabrics impregnated with scent) which may be mixed, heated and/or blown (e.g., via a fan within the fragrance unit 310) to produce a desired fragrance at a desired intensity. The fragrance unit 310 may be powered by a battery. Alternatively, or in addition, the fragrance unit 310 may be powered by electric contacts located on the base 240. The fragrance unit 310 may be controlled via the controller 104.

In some cases the fragrance unit 310 may include a battery and charger circuit to allow the unit to be "charged" via the base 240 and deposited in another location with an environment. The fragrance unit 310 may be remotely controlled via the user device 118 (or controlled indirectly by commands routed through the fan apparatus 102).

Figure 6A:
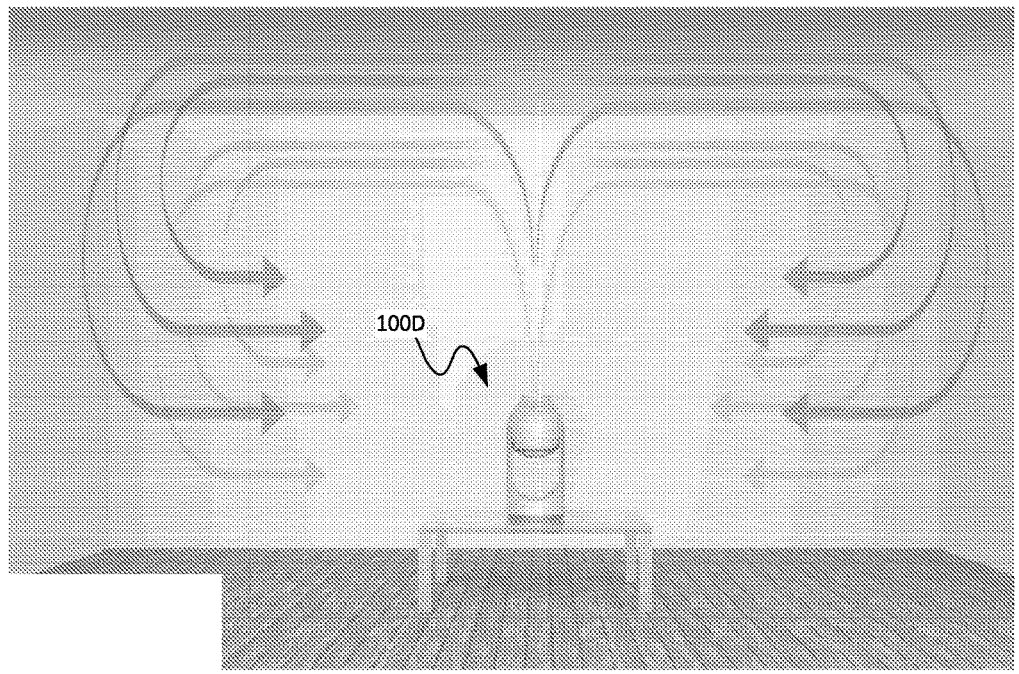
FIG. 6A shows an example air flow within an environment for an example air treatment system in accordance with an embodiment of the present disclosure.

FIG. 6A shows one example embodiment of an air treatment system 100D creating room-wide airflow. In an embodiment, the fan apparatus may point directly/substantially upward and may use one or more image sensors to determine a center of the ceiling. Once determined, a convection current may be identified what circulates hot air that normally stagnates at the top of the ceiling. The fan apparatus 102 may efficiently target such hot/stagnate air and direct cooler air to disrupt the same. Thus stratified layers of air of different temperatures may be mixed efficiently to circulate air fully through an environment.

Figure 6B:
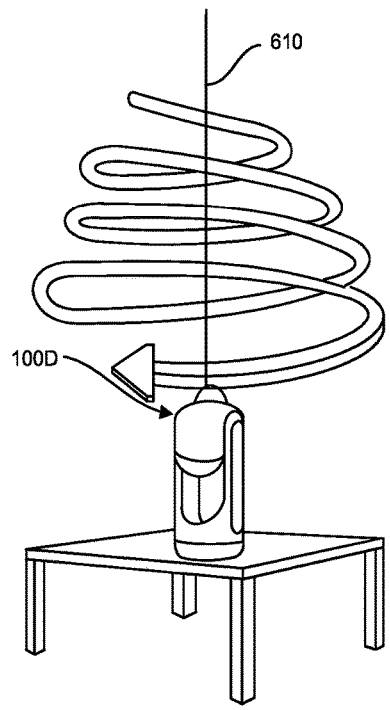
FIG. 6B shows an example air flow within an environment for an example air treatment system in accordance with an embodiment of the present disclosure.

As shown in FIG. 6B another example embodiment of an air treatment system 100D is shown. As shown, the fan apparatus may move in a spiral fashion so as to force hot or stagnant/dirty air from the top layers of an airspace adjacent a ceiling. For example, the fan apparatus may begin facing upwards towards the ceiling and then start by rotating in full continuous revolutions about the base vertical pan axis 610 while slowly tiling down from the upward-facing position. Thus, a spiral may be transcribed by a resulting air stream to force room air downward towards a filter of the air treatment system, for example.

Figure 7:
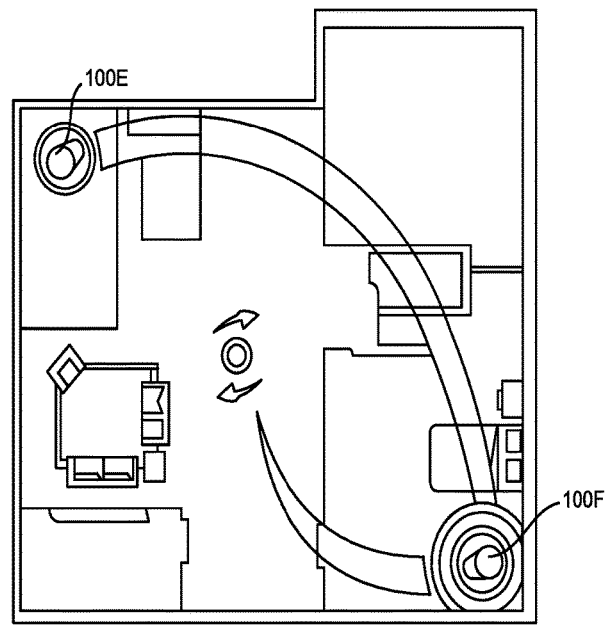
FIG. 7 shows an example of a plurality of air treatment systems communicating with each other in accordance with an embodiment of the present disclosure.

FIG. 7 shows an example embodiment where air treatment system 100E is in communication with air treatment system 100F to provide room-wide/environment-wide circulation. In this embodiment, each air treatments system may share their present direction with each other to ensure that their respective outputs are not directly pointed at each other.

Figure 9:
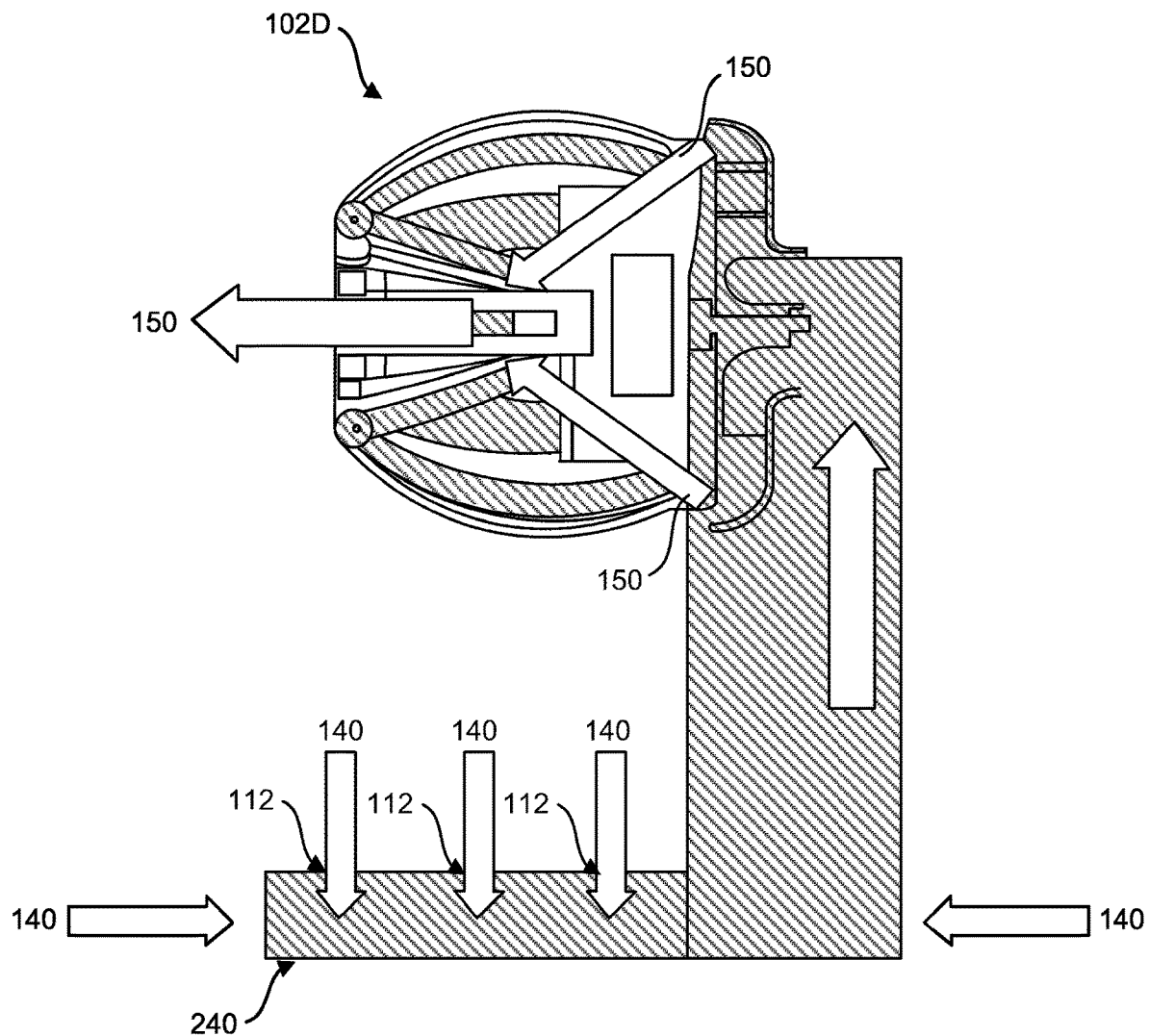
FIG. 9 shows another example embodiment of a fan apparatus, in accordance with an embodiment of the present disclosure.

FIG. 9 shows an example embodiment of a fan apparatus 102D in accordance with an aspect of the present disclosure. As shown, the air is taken in through the base, e.g., via intake 112, and brought up to the spheroid fan portion. A change over valve may then direct air through the spheroid fan portion.

Figure 10:
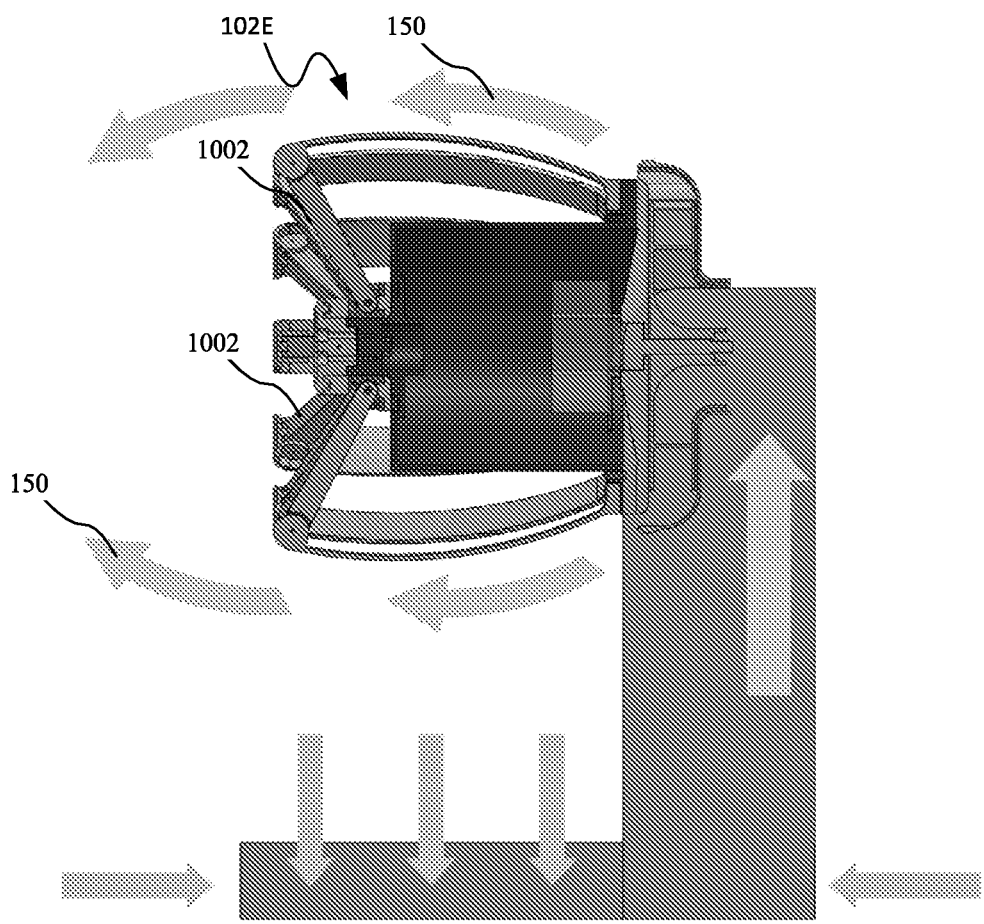
FIG. 10 shows another example embodiment of a fan apparatus, in accordance with an embodiment of the present disclosure.

FIG. 10 shows another example embodiment of a fan apparatus 102E. In this embodiment, hinged elements 1002 allow the spheroid fan portion to "open" similar to a flower to widen an air path for air 150.

Figure 11A:
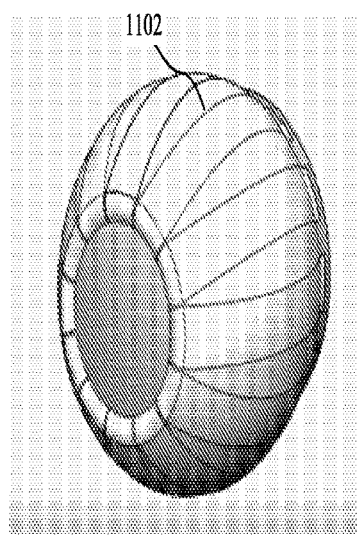
FIGS. 11A-11C shows a plurality of intermediate stages when widening an air path for the fan apparatus of FIG. 10.
Figure 11B:
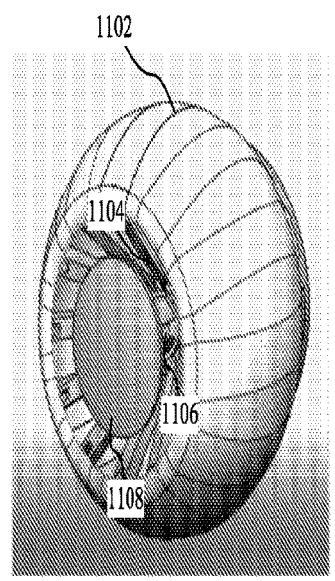
Figure 11C:
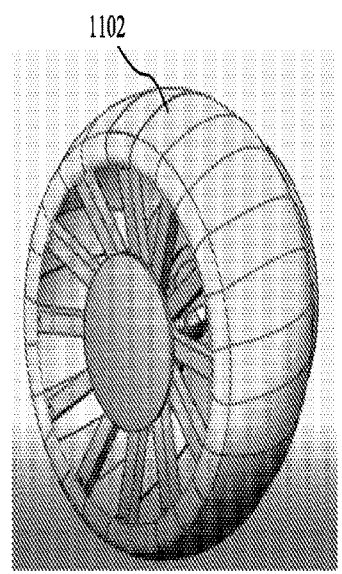
Figure 13A:
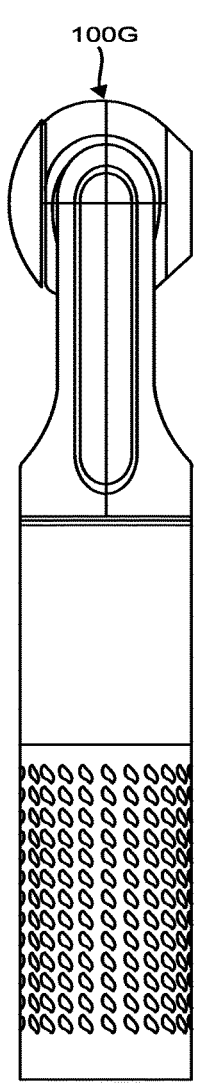
FIGS. 13A-13D show an additional example configuration for an air treatment system, in accordance with an embodiment of the present disclosure.
Figure 13B:
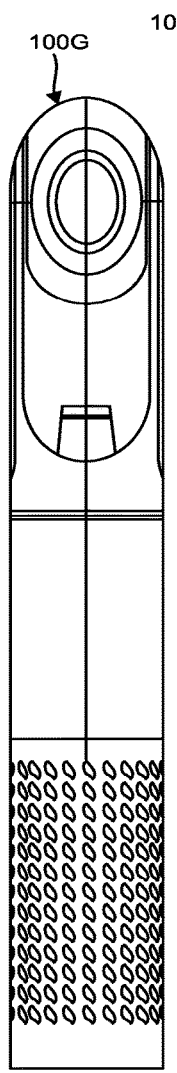
Figure 13C:
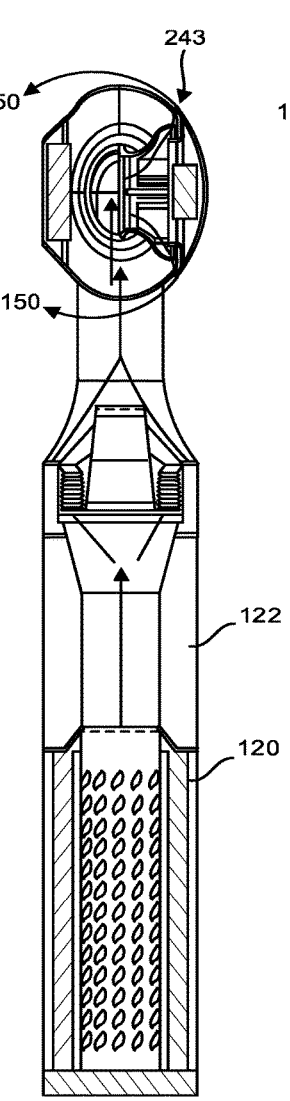
Figure 13D:
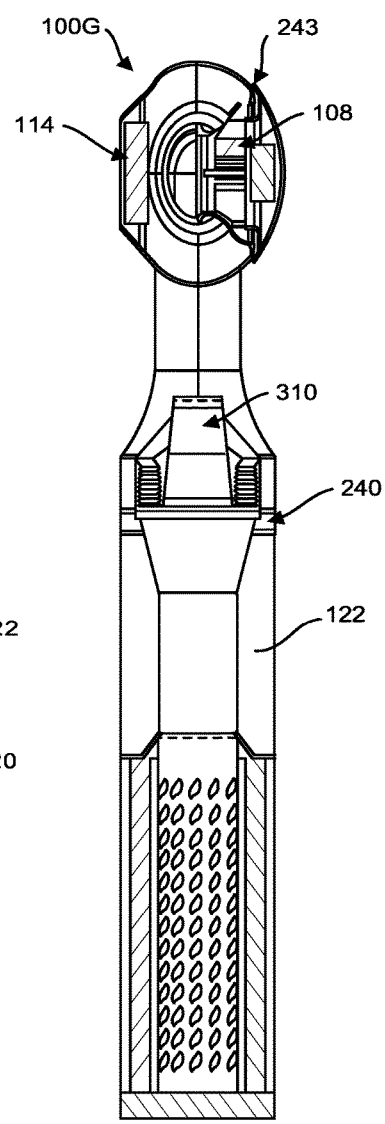
Figure 14A:
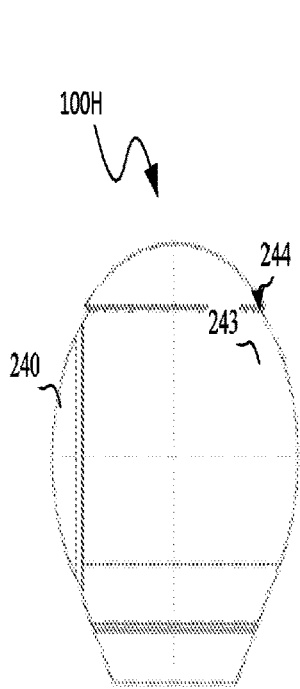
FIGS. 14A-14G show an additional example configuration for an air treatment system, in accordance with an embodiment of the present disclosure.
Figure 14B:
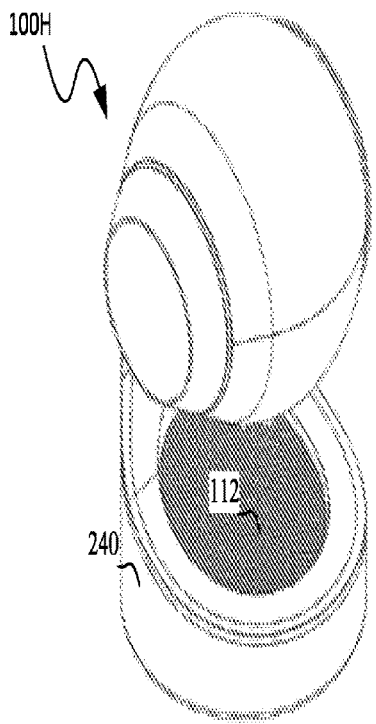
Figure 14C:
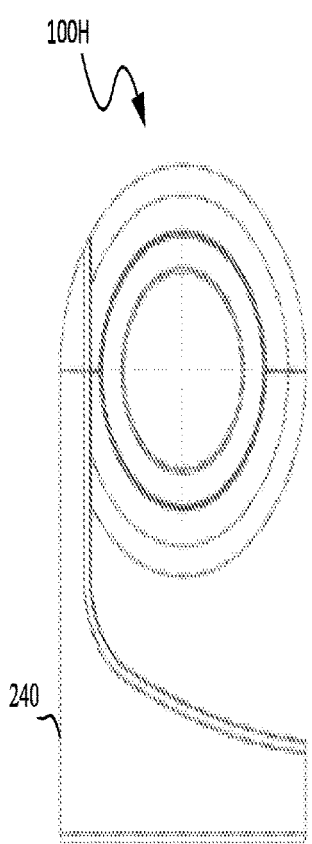
Figure 14D:
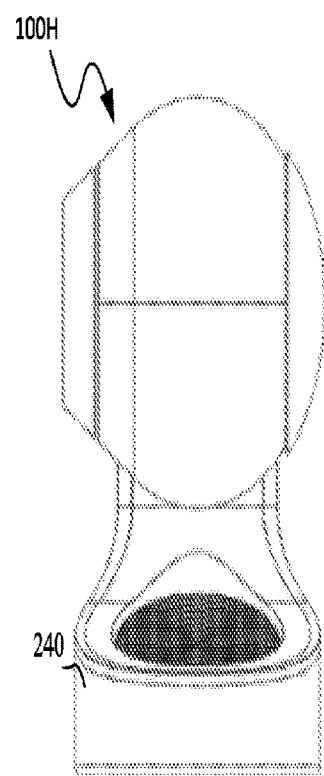
Figure 14E:
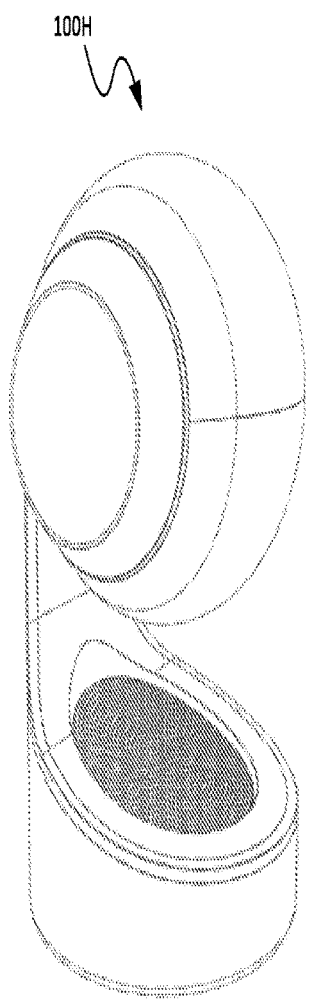
Figure 14F:
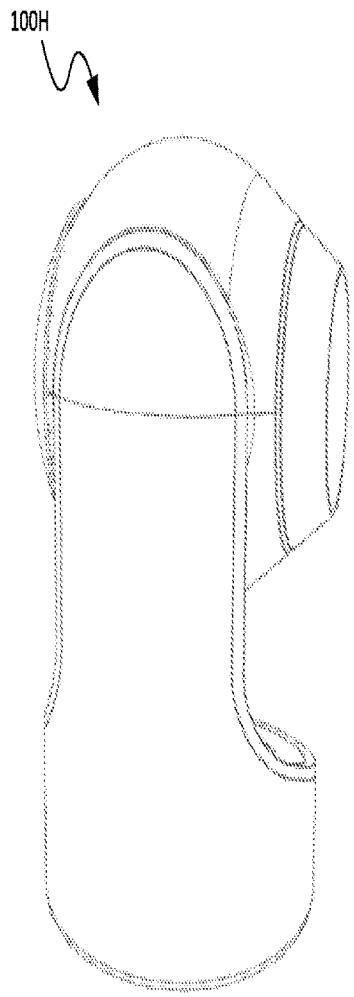
Figure 14G:
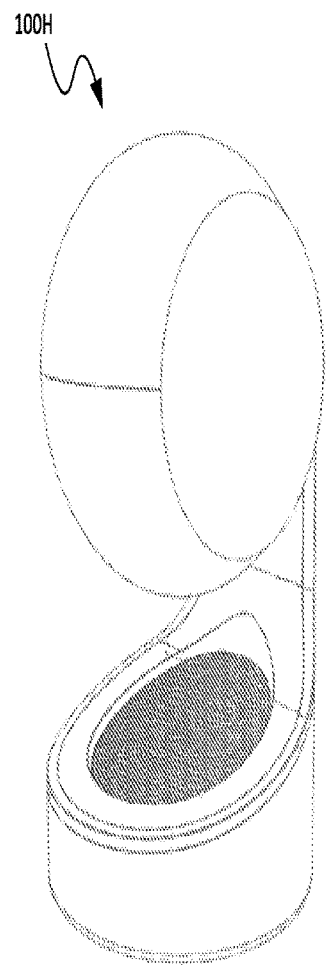

FIGS. 11A-11C show the apparatus 102E of FIG. 10 during various stages of opening/closing. As shown, a stretchable material (e.g., fabric) surrounds the spheroid fan portion. A distal end of the hinged elements 1002 is coupled to a ring 1104 which is concentric about an axle 1106. As the ring 1104 travels towards the disc portion 1108 the spheroid shape widens by function of the hinged elements 1002 extending substantially orthogonal relative to the axle 1106.

As shown in FIG. 11C, this results in a wider spheroid shape relative to the shape shown in FIG. 11A.

FIGS. 12A-12C show an additional configuration in accordance with aspects of the present disclosure. As shown, fan apparatus 102F includes fan inlets within an opening of the base 240.

FIGS. 13A-13D show an additional configuration in accordance with aspects of the present disclosure. As shown, the air treatment system 100G includes an air filter 120 which is in fluid communication with base 240.

FIGS. 14A-14G show an additional configuration in accordance with aspects of the present disclosure. As shown, the air treatment system 100H includes a fan apparatus with a single arm extending from base 240.

Figure 15:
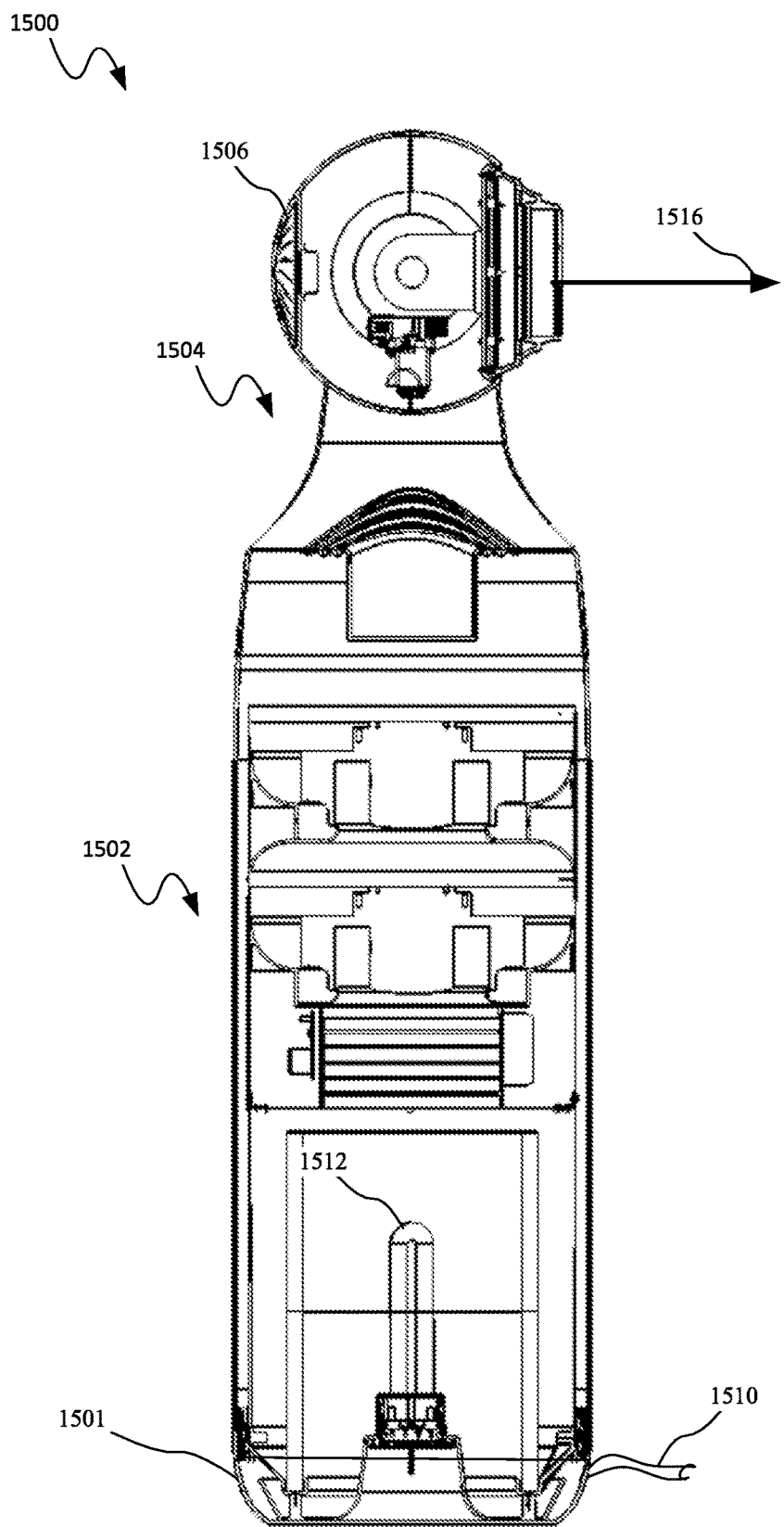
FIG. 15 shows another example air treatment system in accordance with an embodiment of the present disclosure.

FIG. 15 shows another embodiment of a modular air treatment system 1500 consistent with the present disclosure. The proceeding description of the air treatment system 1 and associated figures is equally applicable to the system 1500, and for this reason will not be repeated for brevity.

As shown, the air treatment system includes a base 1501, an air purifier 1502 (or stationary air purification device) and a fan body 1504. The base 1501 may couple to a power source, e.g., AC mains, via a cable 1510. The base 1501 may removably couple to the air purifier 1502. Likewise, the air purifier 1502 may removably couple from the fan body 1504. Note that the fan body 1504 may also directly couple to the base 1501 and the embodiment shown is not intended to be limiting.

The base 1401, the air purifier 1502 and the fan body 1504 may each include associated circuitry, e.g., power conversion circuitry, one or more controllers, a network interface circuit (NIC), and so on. Thus, each of the base 1401, the air purifier 1502, and the fan body 1504 may operate independent of each other. In some cases, each of the components communicates with each other wirelessly using, for instance, short ranged communication such as near-field communication (NFC), Wi-Fi and/or Bluetooth.

The base 1501 may electrically couple to the air purifier 1502 and the fan body 1504. Likewise, the fan body 1504 may electrically couple to the base 1501 by way of the air purifier 1502.

The base 1501 may further be configured to electrically couple to a surface cleaning device, such as a hand-held vacuum, stick vacuum or a robotic vacuum for docking and recharging purposes. For example, the base 1501 may include electrical contacts configured to engage corresponding electrical contacts disposed on the robotic vacuum.

The base 1501 may provide a docking cavity/receptacle (not shown) that allows a surface cleaning device to be at least partially received therein. Therefore, the surface cleaning device may reside between the air purifier 1502 and the base 1501. In a general sense, the docking cavity may act as a garage/storage space for the surface cleaning device. The air purifier 1502 may include a light emitting device 1512, with the light emitting device 1512 configured to emit, for instance, ultraviolet light (e.g., 10 nm to 400 nm wavelengths), to kill harmful bacteria and other microorganisms.

The light emitting device 1512 may be aligned with the docking cavity to provide UV light into the same. In instances where the cleaning device is a robotic vacuum cleaner, the robotic vacuum cleaner may include a light-transmissive surface/region. The light-transmissive surface/region may be configured to receive the UV light emitted from the light emitting device 1512 and pass at least the UV light into a cavity of the robotic vacuum. The cavity of the robotic vacuum may include a filter and a dust cup. Thus, when the robotic vacuum is at least partially received in the docking cavity of the air purifier 1502, the UV light emitted by the light emitting device 1512 may be advantageously used to kill bacteria and odor-causing organisms within the filter and/or dust cup of the robotic vacuum.

A robot vacuum consistent with the present disclosure may include a base, a plurality of wheels coupled to the base, a dirty air inlet defined by the base for receiving dirty air, and a light-transmissive surface disposed on the base. The light-transmissive surface may be configured receive and pass at least wavelengths from 10 nm to 400 nm, i.e., UV light, into a cavity defined by the base. A dust cup may disposed in the cavity, with the dust cup being disposed within a light path extending from the light-transmissive surface into the cavity defined by the base. Alternatively, or in addition, a filter may be disposed in the cavity, with the filter being disposed within a light path extending from the light-transmissive surface into the cavity defined by the base. Accordingly, a filter and/or dust cup of the robotic vacuum may be exposed to UV light to kill microorganisms. UV exposure has shown to increase filter lifespan, and thus, the UV light received within the robotic vacuum may advantageously increase the service life of filters within the robotic vacuum.

Figure 16:
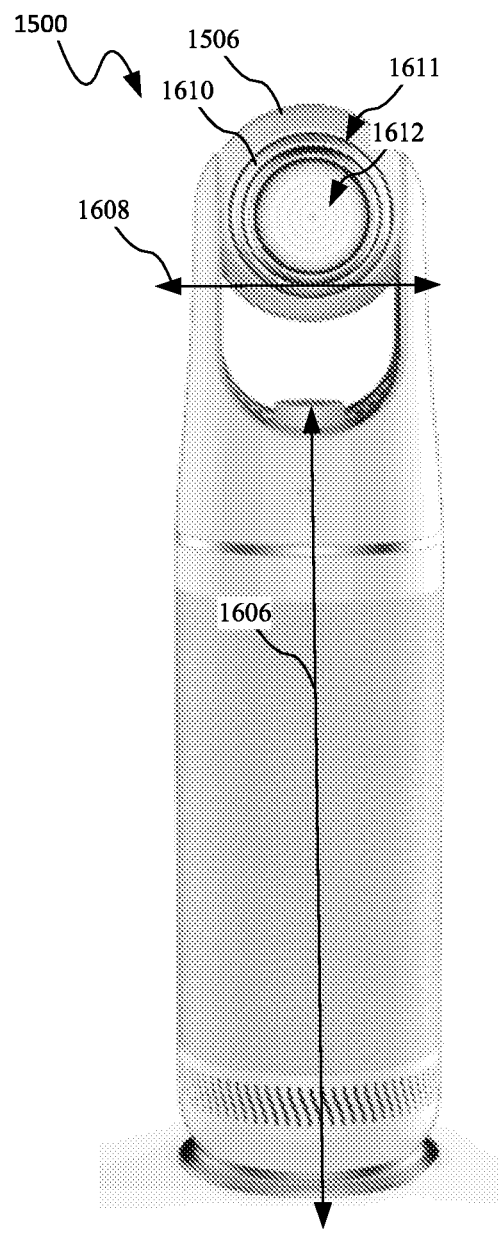
FIG. 16 shows a perspective view of the air treatment system of FIG. 15, in accordance with an embodiment of the present disclosure.

Turning to FIG. 16, a perspective view of the air treatment system 1500 is shown consistent with embodiments of the present disclosure. As shown, the fan head 1506 is configured to rotate about first and second axis, namely, the vertical axis 1606 and the horizontal axis 1608. The fan head 1506 may therefore rotate 360 degrees about each of the first and second axis to provide airflow to a particular area of interest in an environment. As discussed further below, the fan head 1506 may automatically adjust its position during operation based on a real-time control loop (e.g., that uses artificial intelligence/learning routines) or other predefined command sequence. In addition, the fan air treatment system 1500 may provide light, scent and/or humidity to an area of interest. As discussed further below, the fan head 1506 may include a visual indicator that may be utilized to project light on to a wall or other suitable surface. The projected light may convey encoded information such as operational status via simple light patterns. Alternatively, or in addition, the visual indicator may output light similar to a projector to provide shapes, words and/or images on to a surface to convey operational information to a user.

As further shown in FIG. 16, the fan head 1506 includes a nozzle 1610. The nozzle 1610 may include a plurality of openings defined by concentric rings 1611. The total amount of airflow emitted by the nozzle 1610 may be increased relative to nozzles only including a single opening.

The fan head 1506 may further include a visual indicator portion 1612 disposed at about a center of the nozzle 1610. The visual indicator portion 1612 may comprise a plurality of LEDs disposed in, for instance, a circular arrangement/array such as shown. Other LED arrangements are within the scope of this disclosure. Likewise, although the visual indicator portion 1612 is shown as having a circular shape, other shapes are within the scope of this disclosure. The visual indicator portion 1612 may include a light-transmissive cover, e.g., allowing at least 80% of visible wavelengths, emitted by the plurality of LEDs. The light-transmissive cover may be opaque and formed from light-diffusive material. Alternatively, or in addition, the visual indicator portion 1612 may comprise a liquid crystal display (LCD) or other known screen technology.

In an embodiment, the visual indicator portion 1612 includes a lamp, e.g., comprising LEDs or other suitable light emitter that may project on to an adjacent surface, such as a wall, ceiling or object. The projection on the surface may be utilized to convey information to a user such as, for example, operational status, air filtration performance data, diagnostic information, filter health information. Note, the particular surface for the projection may be selected based on sensor data, such as from a proximity sensor, GPS sensor, or any other sensor suitable for determining distances to walls/surfaces.

In any event, the visual indicator portion 1612 may provide a visual indication of the modular air treatment system's operational state. For instance, the visual indicator portion 1612 may emit a blue color when blowing cold air. On the other hand, the visual indicator portion 1612 may emit a red color to indicate airflow that is warm, e.g., based on a heating element (not shown) in the fan head 1506. The visual indicator portion 1612 may also indicate the relative intensity of air flow based on the number of LED rings illuminated. Users may be trained to read the patterns shown by the LED rings.

In an embodiment, the visual indicator portion 1612 may comprise a touch screen or other user interface device that may receive touch/user-input. In some cases, the plurality of concentric rings 1611 may also be configured to receive user-input through capacitance or other known sensing techniques. Thus, a user may adjust operation of the modular air treatment system 1500 by simply touching the plurality of concentric rings 1611 and/or the visual indicator portion 1612. In one specific example embodiment, a user may "slide" one or more fingers along the contours of the plurality of concentric rings 1611 to, for example, adjust airflow intensity up/down. Note, in some cases a user may also use an "app" to communicate with the modular air treatment system 1500 to adjust operation as discussed above with regard to FIG. 1.

FIG. 17A shows an embodiment of the air treatment system 1500 consistent with some embodiments of the present disclosure. As shown, the air treatment system 1500 may direct airflow about a room to create air currents that direct air towards the same for filtering/purification purposes. Thus, the air filtration portion of the air treatment system may remove particulates or otherwise condition the received air.

FIG. 17B and FIG. 17C demonstrate how the fan head 1506 of modular air treatment system 1500 may be detached from the air purifier 1502. In the embodiment shown in FIG. 17C, the fan head 1506 may operate independently of the air purifier 1502. However, the fan head 1506 may communicate, e.g., wirelessly, with the air purifier 1502.

Figures 18A, 18B, 18C:
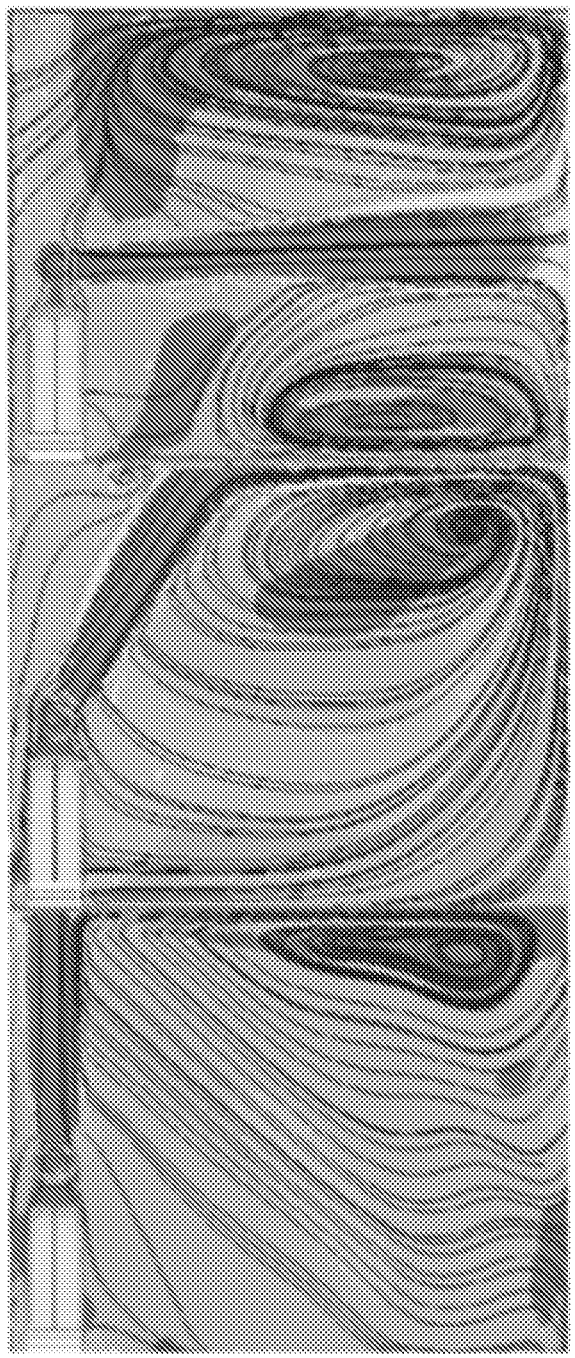
FIGS. 18A-18C show various example airflow patterns of an air treatment system consistent with the present disclosure.

FIGS. 18A-18C show various air flow patterns that the air treatment system 1500 may generate depending on a desired mode of operation in accordance with embodiments of the present disclosure. FIG. 18A shows a parallel airflow pattern whereby the fan displaces air generally along a direction that is parallel with a floor within the surrounding environment. This parallel air flow pattern may generate air currents adjacent the floor and ceiling to cause stale air to circulate and mix with filtered air from the air treatment system 1500.

FIG. 18B shows an upward-angled airflow pattern whereby the fan displaces air generally along a direction that intersects with ceiling, e.g., at an angle of about 45 to 70 degrees relative to the ceiling. This upward-angled airflow may result in a curtain-like effect that cascades from the ceiling to the floor at an end of the room opposite of the modular air treatment system 1500. This curtain effect may advantageously block air from entering in from a doorway or other opening.

FIG. 18C shows a vertical airflow pattern whereby the fan displaces air generally along a direction that is substantially parallel with the longitudinal axis of the modular air treatment system 1500, e.g., at about 90 degrees relative to the ceiling. The vertical airflow pattern may generate relatively uniform air currents throughout the environment surrounding the air treatment system 1500.

Returning to FIG. 15, the air treatment system 1500 may include one or more sensors, e.g., disposed on the fan head 1506 or other location of the fan body 1504. The one or more sensors may comprise at least one of a red-green-blue (RGB) camera sensor, a stereo camera sensor, a global positioning satellite (GPS) sensor, a microphone, a thermal imaging sensor (e.g., an infrared detector), a temperature sensor, a particulate measurement device and/or a humidity sensor.

In an embodiment, the at least one sensor of the air treatment system 1500 may be configured to detect at least one characteristic of the surrounding environment. For instance, the at least one characteristic may comprise room dimensions for the surrounding environment, proximity to one or more walls within the surrounding environment, location of one or more additional air treatment systems relative to the modular air treatment system, a global positioning satellite (GPS) of the modular air treatment system, and/or a thermal map of the surrounding environment (including people and/or animals).

For example, as previously discussed above with regard to FIG. 8, an air treatment system consistent with the present disclosure may utilize an infrared sensor to determine a temperature profile/map of a surrounding environment. In one example scenario, the air treatment system 1500 may be disposed within line-of-sight of a crib or other location where an infant sleeps/rests. The air treatment system 1500 may monitor the infant's temperature and direct warm/cold air flows as necessary to create a comfortable environment for the infant. The air treatment system 1500 may also detect if an infant's temperature is above a threshold that indicates a potential fever. In this case, a message may be sent to a mobile phone or other user device to cause an alert to appear (e.g., a popup screen, an alarm bell, vibration, etc). As discussed in greater detail below, the air treatment system 1500 may also output sound, light, and/or one or more selected scents to create an atmosphere comfortable for infants or room occupants.

The air treatment system 1500 may also utilize similar features when monitoring elderly persons or others who may be bed-ridden. The air treatment system 1500 may detect when, for instance, a target infant/adult is no longer in bed, e.g., by climbing out, falling out of bed, etc. Note, the air treatment system 1500 may utilize data from a plurality of sensors when performing monitoring as described above, e.g., a camera sensor, an infrared sensor, and so on.

In an embodiment, the modular air treatment system 1500 may transition/move the fan head 1506 based on one or more predefined command sequences (or sequences) stored in a memory. Each command sequence may include a plurality of ordered commands to execute during operation, e.g., movements commands to move the fan head 1506, adjust airflow rate and so on.

Likewise, the predefined sequences may be utilized to determine when to switch ON or OFF air purification, adjust flowrates, and so on. In some cases, the sensor data may be utilized when performing a selected predefined sequence. For example, the modular air treatment system 1500 may monitor so-called "foot traffic" to predict/identify areas in an environment most likely to accumulate dust/debris. The air treatment system 1500 may also send messages to a robotic cleaning device while performing a selected sequence to cause the same to also target/focus on the identified areas of interest.

In an embodiment, the air treatment system 1500 may measure cleaning/purifying effectiveness of a selected predefined sequence. For instance, the modular air treatment system 1500 may receive an initial particulate measurement before conducting a selected sequence. After, or during, performance of the selected sequence, the modular air treatment system 1500 may perform one or more additional measurements. The difference between the one more additional measurements and the initial measurement may be utilized to determine effectiveness.

The determined effectiveness may be utilized when performing future selection of a sequence in order to ensure the chosen sequence is optimal for a given environment. Note that the initial particulate measurements may also utilize an outdoor/external measurement as base line. In any event, the modular air treatment system 1500 may include a plurality of remote particle sensor units (or air quality sensors) that may be placed in one or more rooms.

Sensor data from each of the remote particle sensors may be sent, e.g., wirelessly, to the air treatment system 1500 for purposes of determining effectiveness as discussed above.

In an embodiment, the air treatment system 1500 may send data to a remote server that includes information/data representing a selected sequence and the measured effectiveness of the same. The remote server may then aggregate the received data and along with similar data received from other air treatment systems consistent with the present disclosure. For instance, for a given region, data from tens, hundreds, or thousands of air treatment systems may be utilized to determine optimal sequences relative to the particular characteristics peculiar to each environment, e.g., room dimensions, number of units, and so on.

The remote server may utilize statistical analysis, empirical data (e.g., from the sensory, particle detectors, and so on), heuristics, modeling, and/or other suitable approaches to implement a machine-learning process that seeks to identify optimal sequences that may be adjusted over time to continually improve cleaning/purification results.

Thus, in a general sense, an embodiment of the present disclosure includes so-called "crowd sourcing" of information from air treatment systems. The remote server may then send update messages to target air treatment systems to cause the same to add or otherwise modify existing sequences.

In addition, the crowd-sourcing of information may allow for users to understand how their home/office compares to other environments similarly situated. This information may be utilized by a user to understand the amount of pollution in one's environment relative to others and how air-tight their home/office is, or is not, as the case may be. This information may be utilized to present helpful suggestions to a user, e.g., via the "app" discussed above, such as when to increase performance of the air treatment system 1500 to compensate for detected increase in contaminants internal and external to an environment, when to keep windows/doors closed, and whether the performance of their modular air treatment system(s) appears to be on-par with other modular air treatment systems (a filter replacement or other serving may be necessary in the event performance is outside of a predefined threshold). In some cases, the air treatment system 1500 automatically adjusts to compensate for increased amounts of pollution without necessarily requiring user intervention.

Alternatively, or in addition to the sequences discussed above, the modular air treatment system 1500 may implement a real-time movement control loop, which may also be referred to as a real-time control loop. The real-time control loop may be implemented similar to Simultaneous Localization and Mapping (SLAM) whereby the air treatment system 1500 utilizes a series of inputs to modify operational parameters to determine, on a moment-to-moment basis, where to direct air flow and how to work in tandem with other cleaning devices, e.g., a robotic vacuum or other modular air treatment systems within a home/office environment to achieve a desired result. For example, some users may desire a maximum amount of air is filtered so that harmful contaminants are reduced or otherwise eliminated throughout a home/office. Other users may desire to keep air in certain rooms from permeating into others, such as a kitchen space where a user seeks to keep cooking smells contained. Still others may want a system that adapts based on real-life usage to ensure maximum filtration and user comfort.

In any event, the various inputs used by the real-time control loop to adjust operational parameters may include dimensions of the environment surrounding an air treatment system, physical location (e.g., GPS, proximity sensors, and so on) of a unit within the environment, and relative distances between other air treatment systems and/or cleaning devices (e.g., a robotic vacuum). Inputs may further include environment characteristics such as air flow rates, particle counts (e.g., from one or more remote particle counters or an onboard particle detector), temperature (e.g., inside and outdoor temperatures), weather data (e.g., from an Internet source), atmospheric pressure, humidity, image data from one or more camera sensors, and audio samples from one or more microphones, just to name a few.

The real-time control loop may than operate autonomously to make decisions regarding air flow and purification sequences. The real-time control loop may also synchronize with other such real-time control loops running on other air treatment systems disposed about the environment. This synchronization may include sharing the aforementioned sensor data, room dimensions, heat maps, etc. This may allow each real-time control loop to understand the entire topology of a given environment, e.g., room dimensions, position of doors and openings, windows, etc., to create air flows that ensure a maximum amount of air is circulated throughout the environment. Likewise, the real-time control loops may react to real-time changes, e.g., smoke detected from an oven or cooking surface, doors being opened, etc., and adjust air flows to compensate.

The real-time control loop may also perform cleaning/purification effectiveness measurements as discussed above. Therefore, the real-time control loop may utilize sequences that have been "learned" over time to direct air flows, command robotic vacuums, and cycle air purifiers in a manner that maximizes air quality. The real-time control loop may also provide results to a remote server which in turn may aggregate such data as discussed above to determine additional optimizations, new sequences, and so on, that may further increase performance. Thus, the real-time control loop may operate on its own local data/sensors as well as data collected from potentially thousands of other devices to continuously improve performance over time.

In addition, the real-time control loop may detect the presence of users within rooms and adjust air flow in response on the detected users. For instance, the air treatment system 1500 may simply direct air flow at a user if the same detects the user is warmer than average, thus indicating the user was performing strenuous activity (such as working out). In still other cases, the modular air treatment system 1500 may detect the identity of a user based on image data, sound data, thermal imaging, or any combination thereof. Each user may have preferences stored by the modular air treatment system 1500 to allow the same to fine-tune airflow and environmental qualities such as light, sound and smell.

Notably, the air treatment system 1500 is not limited to modifying airflow and air quality, and may also adjust a plurality of mood/environmental qualities (or characteristics). The environmental characteristics may include sight, smell and/or sound. For example, the modular air treatment system 1500 may also adjust light output via the visual indicator portion 1612 to alter the mood of a room. In this example, the visual indicator portion 1612 may output one or more hues to cause a corresponding emotional reaction in a user. The modular air treatment system 1500 may also select a particular scent to output via the fragrance unit 310 (FIG. 3).

The modular air treatment system 1500 may also output sound, e.g., rain drops, music, comfort noise, etc., to effect a user's mood or otherwise provide sounds which are desirable to a user. Any combination of environmental characteristics may be targeted by an air treatment system of the present disclosure. Two or more air treatment systems consistent the present disclosure may synchronize to create a continuous mood throughout a home by adjusting the environmental characteristics discussed above, or may personalize each room/area with different environmental qualities depending on a desired configuration.

At startup an air treatment system 1500 may perform power-on sequences for calibration and diagnostics. The power-on sequence may include a power-on self-test to test various mechanical components, such as motors and components that allow the fan head to pan/tilt. The power-on self-test may also include rotation of the fan head about the horizontal and/or vertical axis of rotation to locate optical interrupts, for instance, thus calibrating the unit automatically at each startup. Other calibration approaches may be utilized.

The power-on sequence for the air treatment system 1500 may further include identifying the position of the same within a given environment. For example, the air treatment system 1500 may use one or more sensors to determine location. In this example, the fan head 1506 may pan/tilt to a number of predefined positions to "learn" its position by visual inspection of its surrounding environment. Visual inspection may therefore utilize for example, a stereo camera sensor and/or CMOS sensor. Alternatively, or in addition, sensors such a GPS sensor, proximity sensor, and so on, may also be utilized to identify location.

The power-on sequence may further include identifying other air treatment systems in the environment, e.g., via Wi-Fi or other short-range communication. The power-on sequence may include sending information to other air treatment systems such as current operational mode, position within the environment, and so on.

An air treatment system consistent with the present disclosure may include a "skin" about its exterior that may be removable or otherwise user-configurable. Thus, a user may select a different color/texture for the body to allow the air treatment system to aesthetically fit within a given environment.

While the principles of the disclosure have been described herein, it is to be understood by those skilled in the art that this description is made only by way of example and not as a limitation as to the scope of the disclosure. Other embodiments are contemplated within the scope of the present disclosure in addition to the exemplary embodiments shown and described herein. It will be appreciated by a person skilled in the art that an air treatment system may embody any one or more of the features contained herein and that the features may be used in any particular combination or sub-combination. Modifications and substitutions by one of ordinary skill in the art are considered to be within the scope of the present disclosure, which is not to be limited except by the following claims.

What is claimed is:

1. A modular air treatment system comprising:
a base;
a fan body to rotatably couple to the base;
a fan head with a nozzle for outputting an airflow within a surrounding environment, the fan head rotatably coupled to the fan body;
wherein the fan body rotates about the base along a first axis of rotation, the first axis of rotation being substantially in parallel with a longitudinal axis of the fan body, and wherein the fan head rotates about the fan body along a second axis of rotation, the second axis of rotation being substantially perpendicular relative to the longitudinal axis of the fan body.

2. The modular air treatment system of claim 1, wherein the first and second axis of rotation collectively allow the nozzle to rotate 360 degrees about the first and second rotational axis to direct air flow at areas of interest within the surrounding environment.

3. A modular air treatment system comprising:
a base;
a fan body to rotatably couple to the base;
a fan head with a nozzle for outputting an airflow within a surrounding environment, the fan head rotatably coupled to the fan body;
wherein the fan head includes at least one sensor to determine at least one characteristic of a surrounding environment, the at least one characteristic comprises room dimensions for the surrounding environment, proximity to one or more walls within the surrounding environment, location of one or more additional modular air treatment systems relative to the modular air treatment system, a global positioning satellite position (GPS) of the modular air treatment system, and/or a thermal map of the surrounding environment.

4. The modular air treatment system of claim 3, wherein the at least one sensor comprises at least one of a red-green-blue depth (RGB-D) camera sensor, a stereo camera sensor, a global positioning satellite (GPS) sensor, a microphone, a thermal imaging sensor, a temperature sensor, a particulate measurement device and/or a humidity sensor.

5. The modular air treatment system of claim 3, wherein the fan head is configured to rotate 360 degrees about a horizontal axis and a vertical axis.

6. A modular air treatment system comprising:
a base;
a fan body to rotatably couple to the base;
a fan head with a nozzle for outputting an airflow within a surrounding environment, the fan head rotatably coupled to the fan body;
wherein the fan head includes at least one sensor to determine at least one characteristic of a surrounding environment, and
wherein the fan head rotates to a plurality of positions about the horizontal and vertical axis to provide airflow within the surrounding environment based at least in part on data from the at least one sensor.

7. The modular air treatment system of claim 6, further comprising a controller to cause the fan head to rotate to the plurality of positions based on a predefined command sequence stored in a memory.

8. The modular air treatment system of claim 7, wherein the controller is configured to measure effectiveness of a first predefined command sequence relative to a second predefined command sequence.

9. The modular air treatment system of claim 8, wherein the controller is configured to measure effectiveness of the first predefined command sequence relative to the second predefined command sequence based on data from one or more particulate sensors.

10. The modular air treatment system of claim 7, wherein the controller is configured to receive a first particulate measurement before performing a predefined command sequence, and a second particulate measurement after or during performance of the predefined command sequence.

11. The modular air treatment system of claim 10, wherein the controller is configured to send a message to a remote server based on a difference between the first and second particulate measurements.

12. The modular air treatment system of claim 7, wherein the controller is configured to receive an update message from a remote server, and in response to receiving the update message, storing and/or modifying a predefined command sequence stored in the memory.

13. The modular air treatment system of claim 7, wherein the controller is configured to send one or more commands to a robotic vacuum cleaner to cause the robotic vacuum to target one or more areas of interest for cleaning purposes.

* * * * *